United States Patent [19]
Matsuno et al.

[11] Patent Number: 6,090,114
[45] Date of Patent: Jul. 18, 2000

[54] TIBIAL PLATEAU RESECTION GUIDE

[75] Inventors: Shigeo Matsuno, Sapporo, Japan; Carlos Esteban Collazo, Ridgefield Park; Stuart L. Axelson, Jr., Succasunna, both of N.J.; Michael Eric Gertner, San Francisco, Calif.

[73] Assignee: Stryker Howmedica Osteonics Corp., Allendale, N.J.

[21] Appl. No.: 09/343,058

[22] Filed: Jun. 29, 1999

Related U.S. Application Data

[63] Continuation-in-part of application No. 08/797,917, Feb. 10, 1997, Pat. No. 5,916,219.

[51] Int. Cl.[7] .................................................... A61B 17/56
[52] U.S. Cl. ............................................. 606/88; 606/86
[58] Field of Search .................................. 606/87, 88, 89, 606/86, 96, 80, 79, 102

[56] References Cited

U.S. PATENT DOCUMENTS

| | | | |
|---|---|---|---|
| 4,211,228 | 7/1980 | Cloutier | 128/303 |
| 4,524,766 | 6/1985 | Petersen | 128/92 |
| 4,567,885 | 2/1986 | Androphy | 128/92 |
| 4,574,794 | 3/1986 | Cooke et al. | 128/92 |
| 4,646,729 | 3/1987 | Kenna et al. | 128/92 |
| 4,736,737 | 4/1988 | Fargie et al. | 128/92 |
| 4,759,350 | 7/1988 | Dunn et al. | 128/92 |
| 4,773,407 | 9/1988 | Petersen | 128/92 |
| 4,787,383 | 11/1988 | Kenna | 128/303 |
| 4,841,975 | 6/1989 | Woolson | 128/653 |
| 4,938,762 | 7/1990 | Wehrli | 606/88 |
| 4,952,213 | 8/1990 | Bowman et al. | 606/79 |
| 5,002,547 | 3/1991 | Poggie et al. | 606/88 |
| 5,342,367 | 8/1994 | Ferrante et al. | 606/86 |
| 5,342,368 | 8/1994 | Petersen | 606/88 |
| 5,451,228 | 9/1995 | Johnson et al. | 606/86 |
| 5,578,039 | 11/1996 | Vendrely et al. | 606/88 |
| 5,628,750 | 5/1997 | Whitlock et al. | 606/88 |
| 5,643,272 | 7/1997 | Haines et al. | 606/88 |
| 5,916,219 | 6/1999 | Matsuno et al. | 606/88 |

OTHER PUBLICATIONS

Publication of Duracon® The Tibial System, Howmedica Inc., Rutherford, NJ, Pfizer Hospital Products Group, ©1993, 1994.

*Primary Examiner*—Gene Mancene
*Assistant Examiner*—Pedro Philogene
*Attorney, Agent, or Firm*—Pennie & Edmonds LLP

[57] ABSTRACT

An apparatus and method for tibial alignment which allows the independent establishment of two separate geometric planes to be used as a reference for the cutting of the tibial plateau during total knee arthroplasty. Two separate frame assemblies with extending rods are coupled to the tibia with a fixed relative angle between them, thereby allowing alignment with the mechanical axis of the bone. A cutting block is mounted on one of the assembly frames and is positioned against the tibia. Stabilizing pins are then placed in the cutting block, allowing the proper tibial plateau resection plane to be created.

22 Claims, 6 Drawing Sheets

TIBIAL PLATEAU RESECTION GUIDE

This is a continuation-In-Part of application Ser. No. 08/797,917 filed Feb. 10, 1997 now U.S. Pat. No. 5,916,219.

1. FIELD OF THE INVENTION

The present invention is directed to an apparatus useful as a tibial plateau resection guide and methods for its use in arthroplastic surgery of the knee. More particularly, the invention relates to an apparatus which utilizes adjustable rods in order to fix a bone saw guide to the anterior portion of a patient's proximal tibia.

2. BACKGROUND OF THE INVENTION

In replacing the knee joint which has been damaged due to disease or trauma, it is important that the damaged bone at the proximal end of the tibia be removed by cutting it at an appropriate varus/valgus angle and at an appropriate flexion/extension angle. In this manner, the bone cut will be in the correct varus/valgus and flexion/extension alignment, and the proximal end of the tibia can then receive an implant or prosthesis to reconstruct a functioning knee joint. Proper fit and function of the implant will depend on the accuracy of the cut.

Many devices for determining the correct angle of the bone cut are known in the art. The known devices typically include a cutting block which guides a saw blade and an anterior telescoping rod or similar device which extends to a position adjacent the approximate center of the anterior face of the patient's ankle or talus to allow the surgeon to duplicate the mechanical axis of the tibia as a reference guide for the proper alignment of the cutting block with the mechanical axis.

Johnson et al., U.S. Pat. No. 5,451,228 (Johnson) discloses a tibial resector guide having an angularly adjustable head controlled by a thumb actuated slide mechanism. The tibial resector guide disclosed by Johnson includes only one telescoping rod to reference the mechanical axis, but no external side rod or similar means to reference the mid-coronal plane.

Ferrante et al., U.S. Pat. No. 5,342,367 (Ferrante) discloses a tibial cutting guide which does not include any means for external referencing, such as extending rods.

Bowman et al., U.S. Pat. No. 4,952,213 (Bowman) discloses using an intramedullary rod connected to a pivot device carrying the bone saw guide. There is no external referencing rod disclosed in Bowman—rather, the reference used is the intramedullary rod inserted deep into the bone canal.

Petersen, U.S. Pat. No. 5,342,368 (Petersen '368) discloses a proximal tibial resector guide including an intramedullary rod which is attached at its proximal end to a bar provided for the cutting saw guide. There is no external referencing rod disclosed in Peterson—rather, the reference used is the intramedullary rod inserted deep into the bone canal.

Petersen, U.S. Pat. No. 4,524,766 (Petersen '766) discloses a surgical knee alignment system including a tibial resection saw guide which is mounted on one telescoping external rod used to reference the mechanical axis. There is no external side rod or similar means disclosed to reference the mid-coronal plane.

Petersen, U.S. Pat. No. 5,395,377 (Petersen '377) discloses an extramedullary proximal tibial guide that includes a distal end carrying a vertically adjustable ankle bracket as well as an ankle pointer, and a proximal end carrying a saw guide. There is no external side rod or similar means disclosed to reference the mid-coronal plane.

Wehrli, U.S. Pat. No. 4,938,762 (Wehrli) discloses a reference system for the implantation of condylar total knee prostheses, including a tibial resection saw guide. The Wehrli system utilizes as a main reference point a screw placed in the pelvis, and includes a number of screws placed into the tibia. Telescoping rods attached to the pelvic bone screw and the tibial bone screw are utilized to position the tibial resection saw guide.

A drawback of the use of intramedullary rods as references is that the anatomy of many patients does not permit an intramedullary rod to be fully inserted.

Also, with both intramedullary and extramedullary tibial resection guides, a drawback of the use of a single, anterior guide rod is that the surgeon lacks a side reference guide to provide a means of reliably and accurately referencing the mid-coronal plane. The present invention addresses this need by providing both anterior and side guide rods to reference both the mechanical axis and mid-coronal plane.

Additionally, during total knee replacement surgery, the patella is normally everted to the lateral side of the knee which may interfere with a side referencing rod. The present invention provides a side referencing frame that is attached to the first distally extending guide rod assembly anteriorly to the patella, thus allowing lateral placement without interfering with the patella, while at the same time allowing multiple planes to be referenced during alignment, such as the mid-coronal plane or longitudinal axis of the fibula, while maintaining a constant angle to the plane of resection.

Citation or identification of any reference in Section 2 or any section of this application should not be construed as an admission that such reference is available as prior art to the present invention. The teachings of these patents are incorporated by reference herein.

3. SUMMARY OF THE INVENTION

The present invention is directed to an apparatus useful as a tibial plateau resection guide and methods for its use in arthroplastic surgery of the knee. The apparatus has an alignment system that allows for the independent establishment of two separate geometric planes to be used for the accurate placement of a cutting guide for use in removing damaged bone at the proximal end of the tibia during knee arthroplasty. The axis formed by the intersection of these two planes is intended to duplicate the mechanical axis of the tibia. An angular relationship between the bone and the cutting block is established by fixing a number of adjustable parameters, thereby allowing a surgeon to make a cut in the transverse plane of the tibia at specific, preferred varus/valgus and flexion/extension angles relative to the duplicated mechanical axis.

The present invention consists of a first and second guide rod assembly with the second distally extending guide rod assembly attached to the first distally extending guide rod assembly anteriorly to the patella, thus allowing lateral placement without interfering with the patella. A side extending rod, used for flexion/extension alignment of the cutting instrument, is adjustable in the anterior-posterior direction, thus allowing multiple planes to be referenced during alignment, such as the mid-coronal plane or longitudinal axis of the fibula while maintaining a constant angle to the plane of resection.

In one embodiment, the apparatus of the present invention comprises an inverted L-shaped first distally extending guide rod assembly placed in the sagittal plane and a reversed L-shaped second distally extending guide rod assembly placed in the transverse plane to which a slidably attached side bar is perpendicularly coupled. The two frame assemblies are coupled to one another, preferably removably coupled, preferably below the tibial plateau, at a constant angle to one another (e.g., 90 degrees). The first distally extending guide rod assembly, which is placed in the sagittal plane, has a first end and a second end, and has a pivot block, a pivot arm, a support arm, a removably attached cutting block (cutting saw guide) and a telescoping rod which can be extended to the center of the anterior face of the distal end of the tibia, i.e., the center of the talus or ankle. The second distally extending guide rod assembly placed in the transverse plane has a first end and a second end, and has a side bar, a top bar and a rod which can be slidably extended through the side bar to the center of the subject's malleolus.

In use, the two interlocking frame assemblies are assembled together, one adjacent the anterior portion of the tibia and one adjacent either the lateral or medial portion of the tibia. The frame assemblies may be assembled prior to anchoring the assemblies or the second distally extending guide rod assembly may be combined with the first distally extending guide rod assembly after the first distally extending guide rod assembly has been secured to the tibia. While the surgeon may secure both frame assemblies to the tibia after they have already been coupled, it is anticipated that most surgeons will secure the first distally extending guide rod assembly first, followed by attaching the second distally extending guide rod assembly to the first distally extending guide rod assembly. Most surgeons prefer to position the second distally extending guide rod assembly on the lateral side, or the outer of the leg, rather than the medial side, or the inner side of the leg, to reference the fibular axis. However, the present invention may be adapted for the second distally extending guide rod assembly to be used on either the lateral or medial side of the tibia.

The first distally extending guide rod assembly may be secured to the tibia in various manners. In one embodiment, the pivot block may be anchored to the proximal end of the tibia by means of a primary pin inserted approximately into the intramedullary canal area. In another embodiment, the anchor block may be anchored by tamping securing pins on the anchor block into the tibia. Alternatively, a hole may be drilled in the proximal end of the tibia in the location of the intramedullary canal. An intramedullary rod may then be placed through the pivot block into the intramedullary canal to anchor the guide assembly. In yet another embodiment, the first distally extending guide rod may be anchored through pins inserted through the cutting block.

Where the first distally extending guide rod assembly is anchored above the tibial plateau, the frontal telescoping rod is then extended downward and rotated using a rod hinge in the required direction until the end of the rod is placed directly over the end of the tibia. The rod hinge can then be maintained in a fixed position by turning a thumb screw. The pivot block is fixed in place by means of a secondary pin which anchors it to the tibial plateau and prevents the apparatus from rotating. A cutting block is removably attached, either at a fixed or at an adjustable angle, to a proximal portion of the first distally extending guide rod assembly. Adjustments to the angle of each frame assembly and to the height of the cutting block can be made and locked into place.

The two frame assemblies have a fixed angle between them. In the preferred embodiment, the fixed angle between the frame assemblies is 90 degrees, thereby providing direct and reliable references to the mid-coronal plane and to the mechanical axis. This facilitates the identification of the tibial mechanical axis. However, the angle may vary according to the preference of the user.

The present invention also provides for a method of using the tibial resection guide in knee arthroplasty. The method includes attaching a first frame assembly to the tibia and coupling a second frame assembly to the first assembly which interlocks the assemblies, preferably at angle of 90 degrees. A frontal telescoping rod which extends downwards from the first distally extending guide rod assembly is placed adjacent to the approximate center of the distal end of the tibia or talus. A slidably attached rod which extends downwards from the second distally extending guide rod assembly is placed in the approximate center of the malleolus. In order to set the extending rod in the center of the malleolus, the surgeon may have to slide the extending rod along the top bar of the second distally extending guide rod assembly. A stylus is then used to measure the resection guide height.

4. BRIEF DESCRIPTION OF THE FIGURES

5. DETAILED DESCRIPTION OF THE INVENTION

Figure 3:
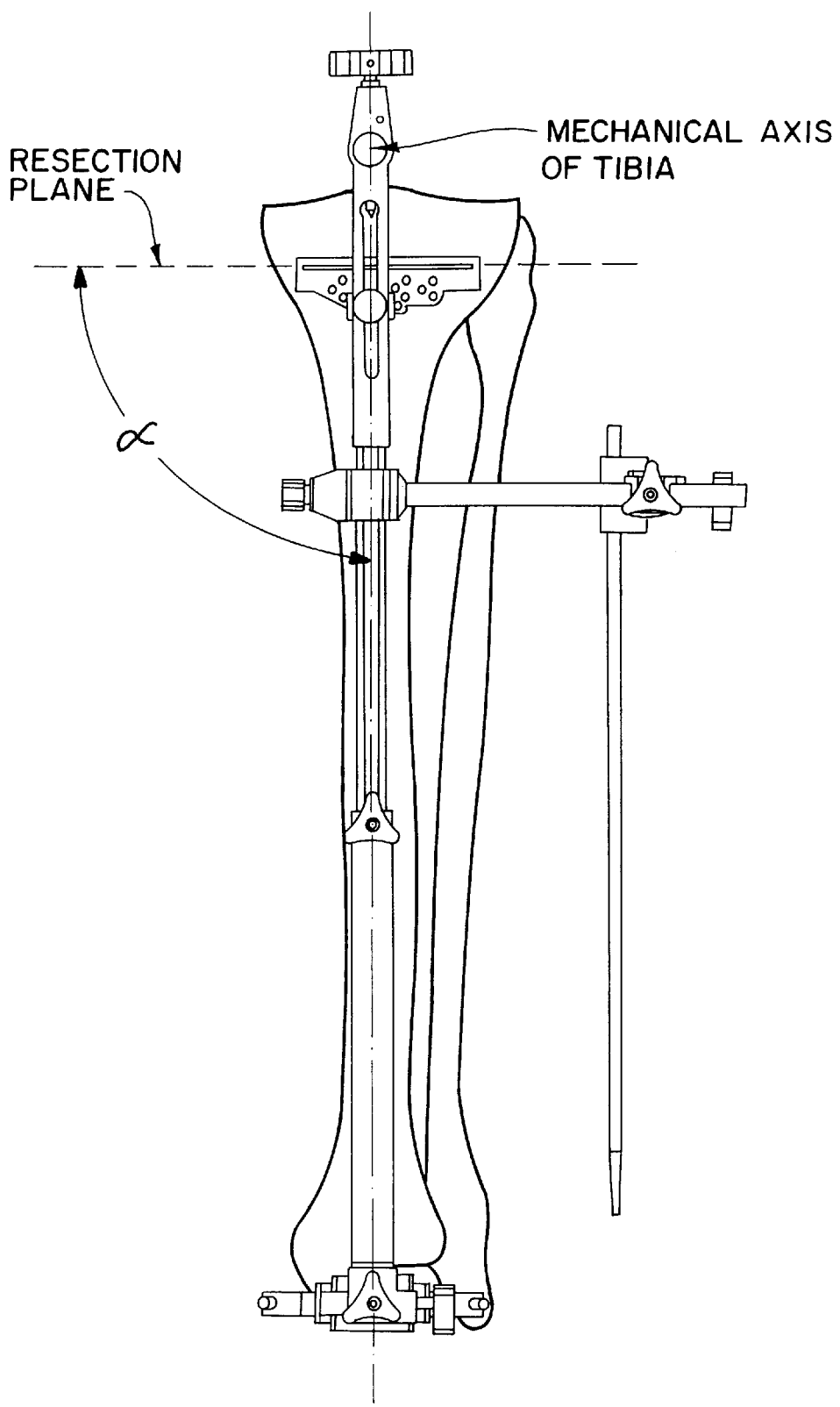
FIG. 3 is an anterior view of a tibia and fibula showing the positional relation of the mechanical axis with respect to the resection plane and to the first distally extending guide rod assembly.
Figure 4:
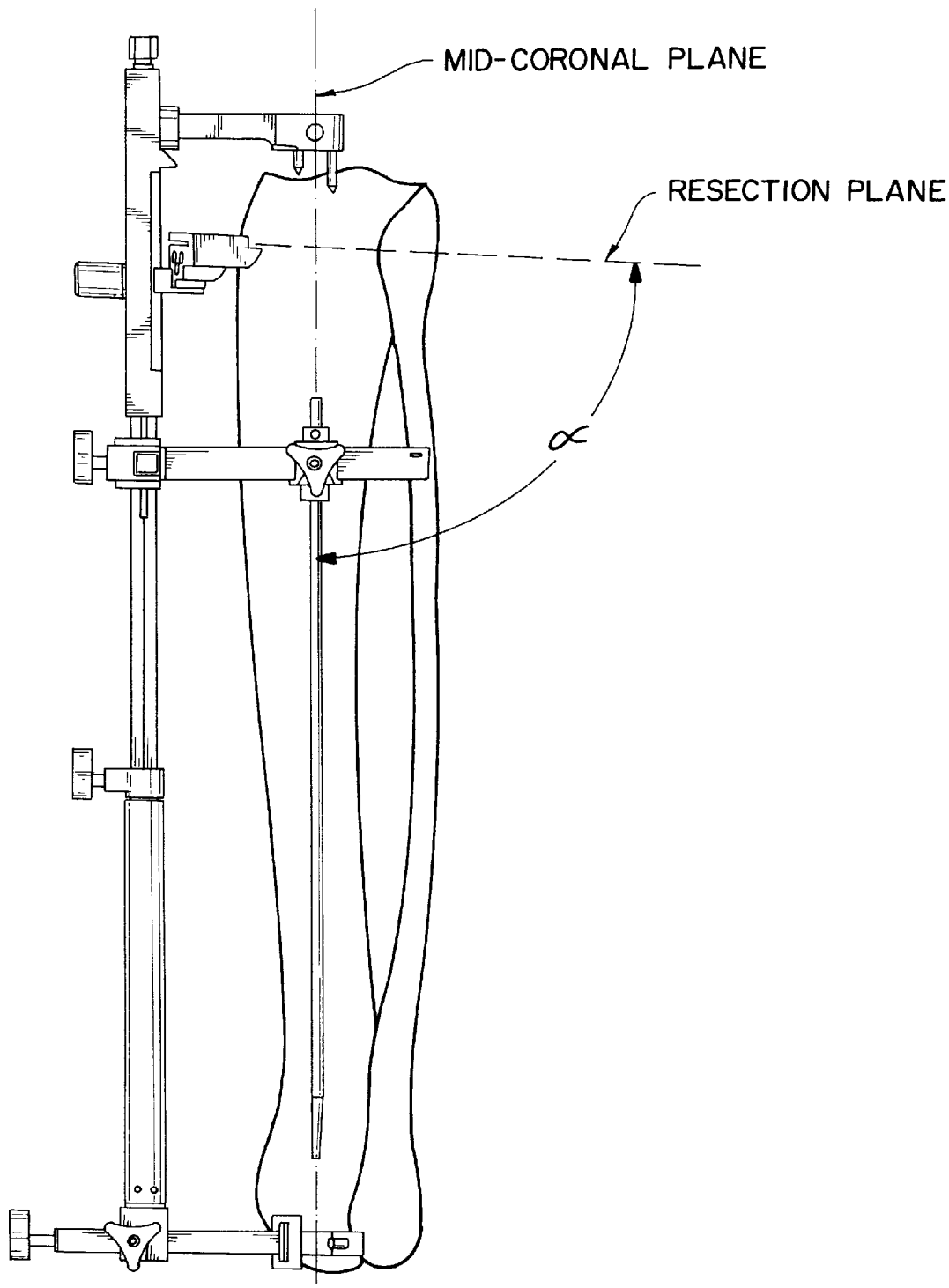
FIG. 4 is a side view of a tibia and fibula showing the positional relation of the mid-coronal plane with respect to the resection plane and to the reference rod of the second distally extending guide rod assembly.

The present invention is directed to a tibial alignment system that allows the independent establishment of two separate geometric planes to be used for angular reference in the cutting of the tibial plateau during partial or total knee arthroplasty. The reference planes intersect one another at a fixed relative angle. The axis formed by the intersection of these two planes is intended to duplicate the mechanical axis of the tibia, which represents an imaginary line connecting the approximate center of the proximal and distal ends of the bone. A predetermined angular relationship between the reconstructed mechanical axis (see FIG. 3) and the resection plane (see FIG. 3), defined by the surface of the cutting block, determines the specific varus/valgus angle of the bone cut. Additionally, a predetermined angular relationship between the mid-coronal plane (see FIG. 4) and the resection plane (see FIG. 4) determines the specific flexion/extension angle of the bone cut. By determining these angles the surgeon can resect the tibia optimally to allow for the most precise fit of a knee prosthesis, maximizing the performance, comfort and wear of the prosthesis.

Figure 1:
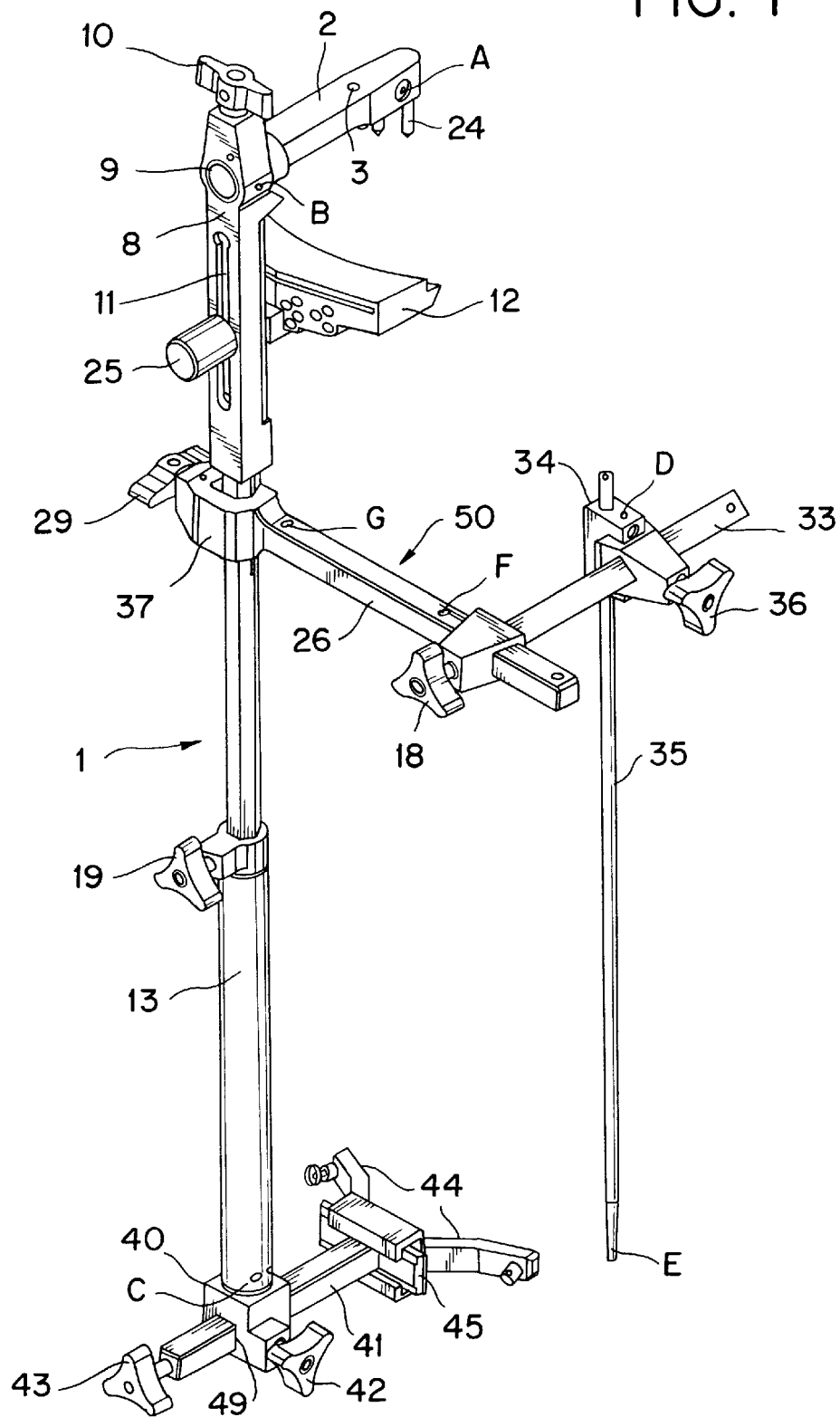
FIG. 1 is a perspective view of one type of Extra Medullary Tibial Resection Guide.

FIG. 1 shows a preferred embodiment of extramedullary tibial resection guide. In this embodiment, preaffixed securing pins (24) anchor the first distally extending guide rod assembly (1) to the top of the tibia. The first distally extending guide rod assembly (1) is composed of four main elements: anchor block (2), support arm (8), cutting block (12), and frontal telescoping rod (13). In this embodiment the securing pins (24) are affixed to the anchor block (2). The anchor block (2) is attached to the support arm (8). After the surgeon has positioned the cutting block (12) in close proximity to the front of the tibia and in the desired orientation, a secondary anchor pin (not shown) is placed in a secondary hole or aperture (3) to secure the entire first distally extending guide rod assembly (1) in place. The sagittal reference plane where the first distally extending guide rod assembly (1) lies is defined by points A, B, and C. Point A lies in the approximate center of the tibial plateau, point B is the intersection of the support arm (8) and anchor block (2), and point C lies at the distal tip of the frontal telescoping rod (13), which is placed at the approximate center of the anterior face of the distal end of the tibia or ankle.

The anchor block (2) fits into the aperture (9) on the support arm (8) and locked in place with a thumbscrew (10). The support arm (8) has an elongated aperture (11) in the approximate center of the support arm (8). A screw (25) fits through the elongated aperture (11) and allows for the tightening of the cutting block (12) against the support arm (8). This allows the cutting block (12) to be stabilized at an optimal position along the tibia based on where the surgeon determines the cut should be made. A stylus (not shown) is used to set the depth of the cut at the level desired by the surgeon.

The support arm (8) is attached at its distal end to a frontal telescoping rod (13) which has an adjustable length. The frontal telescoping rod (13) can be fixed at a position to adjust the length of the first distally extending guide rod assembly (1), as determined by the surgeon, by tightening a thumbscrew (19). The distal end of the telescoping rod (13) may be secured to the ankle through ankle clamp (40) which is affixed to the distal end of the telescoping rod (13). The ankle clamp (40) is adjustable to contact the ankle by sliding the ankle clamp rod (41) through an aperture (49) and can be fixed in place by tightening a thumbscrew (42). The ankle clamp attachments (44) can be horizontally moved on the end (45) of ankle clamp rod (41) to best adjust to the ankle and can be fixed in place with a thumbscrew (43). The second distally extending guide rod assembly (50) is removably attached to the first distally extending guide rod assembly (1) and is secured thereon by an attachment lever or a thumbscrew (29).

The second distally extending guide rod assembly (50) is made up of several parts, including: side bar (26); connection (37); top bar (33); rod anchoring block (34); and an extending rod (35). The second distally extending guide rod assembly (50) has a side bar (26) with a first end and second end.

The side bar (26) is connected to the first distally extending guide rod assembly (1) at its first end through a connection (37) that may be a c-clamp type connection such as that shown. Alternatively, side bar (26) may have a dovetail connection (such as in FIG. 2 (217)) to engage grooves (see FIG. 2 (238)) of the support arm (8) below the cutting block (12). With this variation, the anterior half and posterior half of the grooved members (see FIG. 2, grooved members (227) and (228)) are connected to a thumbscrew or lever arm such that turning the thumbscrew or activating the lever arm causes the anterior half and posterior half to close on the dovetail connection of the side bar, gripping it in place.

At its second end, the side bar (26) is connected to top bar (33), which extends perpendicularly in the transverse plane from the side bar (26), the transverse plane being defined by points D, F, and G. The top bar (33) has a first end and a second end. The first end of the top bar (33) is connected to the side bar (26). The top bar (33) may slide back and forth on the side bar (26) in the coronal plane to adjust the distance of the top bar (33) from the leg of the patient. The coronal reference plane being defined by points A, D, and E. Point A lies on the approximate center of the tibial plateau at the very top of the tibia. Point D lies at the top of a rod anchoring block (34). Point E lies at the distal end of an extending rod (35), at the approximate center of the malleolus.

The top bar (33) may be secured at a position on the side bar (26) by tightening a thumbscrew (18) or a similar functioning lever arm. Proximate the second end of the top bar (33) a rod anchoring block (34) is connected thereto. The rod anchoring block (34) may slide on the top bar (33) to adjust its position thereon.

The proximal end of an extending rod (35) which extends downwardly perpendicular to the top bar (33) is slidably coupled to the proximal end of the rod anchoring block (34). In order to facilitate the placement of the distal end of the extending rod (35) adjacent the malleolus, the surgeon may slide the top bar (33) along the side bar (26) and/or slide the rod anchoring block (34) along the top bar (33) which merely varies the position of the distal end of the extending rod (35) and does not affect any other parameter. When the distal end of the extending rod (35) is brought in close proximity to the approximate center of the malleolus on the lateral face of the distal end of the tibia, thumbscrews (18) and (36) may be tightened to secure the position of the extending rod (35).

Figure 2:
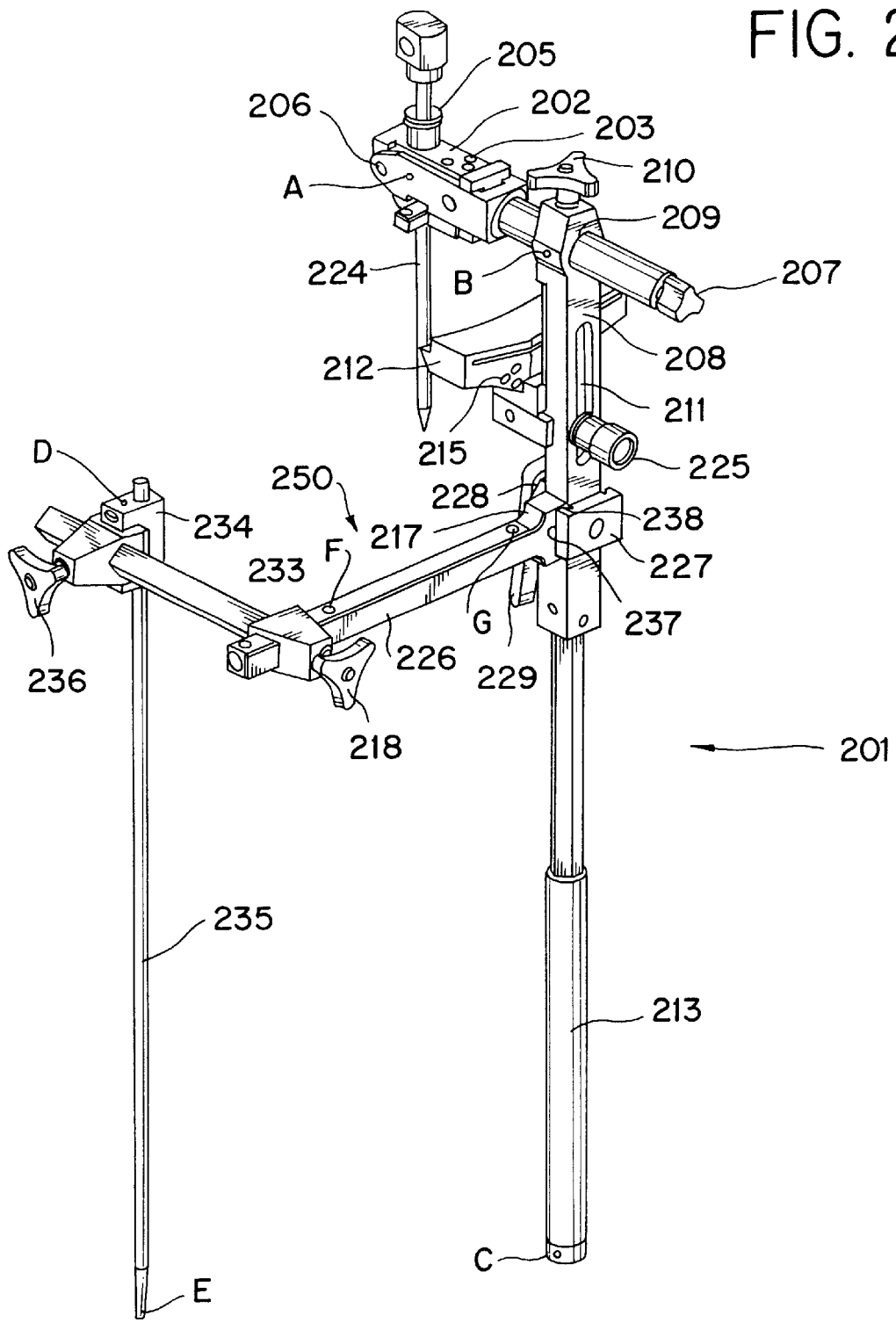
FIG. 2 is a perspective view of another type of Extra Medullary Tibial Resection Guide.

FIG. 2 shows an alternative preferred embodiment of an extramedullary tibial resection guide. In this embodiment, a primary anchor pin (224) anchors the assembly to the approximate center of the top of the tibia. The first distally extending guide rod assembly (201) is composed of five main elements: pivot block (202), pivot arm (204), support arm (208), cutting block (212), and frontal telescoping rod (213).

In this embodiment the primary anchor pin (224) runs through the pivot block (202) at a hole or aperture (205). The pivot block (202) itself is pivotally attached to the posterior end of the pivot arm (204) near a hinge point (206), which allows rotation of the pivot arm about the axis in the direction of the sagittal plane. Additionally, the pivot block (202) and attached pivot arm (204) can swivel about hole (205) after the insertion of the primary anchor pin (224). After the surgeon has positioned the cutting block (212) in close proximity to the front of the tibia, a secondary anchor pin (not shown) is placed in secondary hole or aperture (203) to secure the entire first distally extending guide rod assembly (201) in place. At the anterior end of the pivot arm (204), a thumbscrew or lever (207) can be turned to tighten the grip of the pivot arm (204) against the pivot block (202).

The pivot arm (204) extends through the aperture (209) of the support arm (208) and may slide back and forth on the pivot arm (204), and is tightened against the pivot arm by a thumbscrew (210) or similarly functioning lever located adjacent the aperture (209). The support arm (208) has an elongated aperture (211) in the approximate center of the support arm (208). A screw (225) fits through the elongated aperture (211) and allows for the tightening of the cutting block (212) against the support arm (208). This allows the cutting block (212) to be stabilized at an optimal position along the tibia based on where the surgeon determines the cut should be made. A stylus (not shown) is used to set the depth of the cut at the level desired by the surgeon.

The support arm (208) is attached at its distal end to a frontal telescoping rod (213) which can adjust the length of the first distally extending guide rod assembly (201). Alternatively, the frontal telescoping rod (213) can be fixed at a position determined by the surgeon by tightening a thumbscrew (see FIG. 1 thumbscrew (19)). Optionally, the distal end of the first distally extending guide rod assembly (201) may be secured to the ankle through an ankle clamp assembly such as that shown in FIG. 1 where an ankle clamp (40) would be affixed to the distal end of the first distally extending guide rod assembly (201).

The second distally extending guide rod assembly (250) is made up of several parts, including: side bar (226); connection (237); top bar (233); rod anchoring block (234); and an extending rod (235). The second distally extending guide rod assembly (250) has a side bar (226) with a first end and second end.

The side bar (226) is connected to the first distally extending guide rod assembly (201) at its first end through a connection (237) that may be a dovetail connection (217) to engage grooves (238) of the support arm (208) below the cutting block (212). With this type of connection, the anterior half (227) and posterior half (228) of the grooved members are connected to a thumbscrew or lever arm (229) such that turning the thumbscrew or activating the lever arm (229) causes the anterior half (227) and posterior half (228) to close on the dovetail connection (217) of the side bar (226), gripping it in place. Alternatively, the side bar (226) may be connected to distally extending guide rod assembly (201) through a c-clamp connection as described above in FIG. 1 and as displayed in FIG. 5.

At its second end, the side bar (226) is connected to top bar (233), which extends perpendicularly in the transverse plane from the side bar (226), the transverse plane being defined by points D, F, and G. The top bar (233) has a first end and a second end. The first end of the top bar (233) is connected to the side bar (226). The top bar (233) may slide back and forth on the side bar (226) in the coronal plane to adjust the distance of the top bar (233) from the leg of the patient. The coronal reference plane being defined by points A, D, and E.

The top bar (233) may be secured at a position on the side bar (226) by tightening a thumbscrew (218) or a similar functioning lever arm. Proximate the second end of the top bar (233) a rod anchoring block (234) is connected thereto. The rod anchoring block (234) may slide on the top bar (233) to adjust its position thereon.

The proximal end of an extending rod (235) which extends downwardly perpendicular to the top bar (233) is slidably coupled to the proximal end of the rod anchoring block (234). In order to facilitate the placement of the distal end of the extending rod (235) adjacent the malleolus, the surgeon may slide the top bar (233) along the side bar (226) and/or slide the rod anchoring block (234) along the top bar (233) which merely varies the position of the distal end of the extending rod (235) and does not affect any other parameter. When the distal end of the extending rod (235) is brought in close proximity to the approximate center of the malleolus on the medial face of the distal end of the tibia, thumbscrews (218) and (236) may be tightened to secure the position of the extending rod (235).

Figure 5:
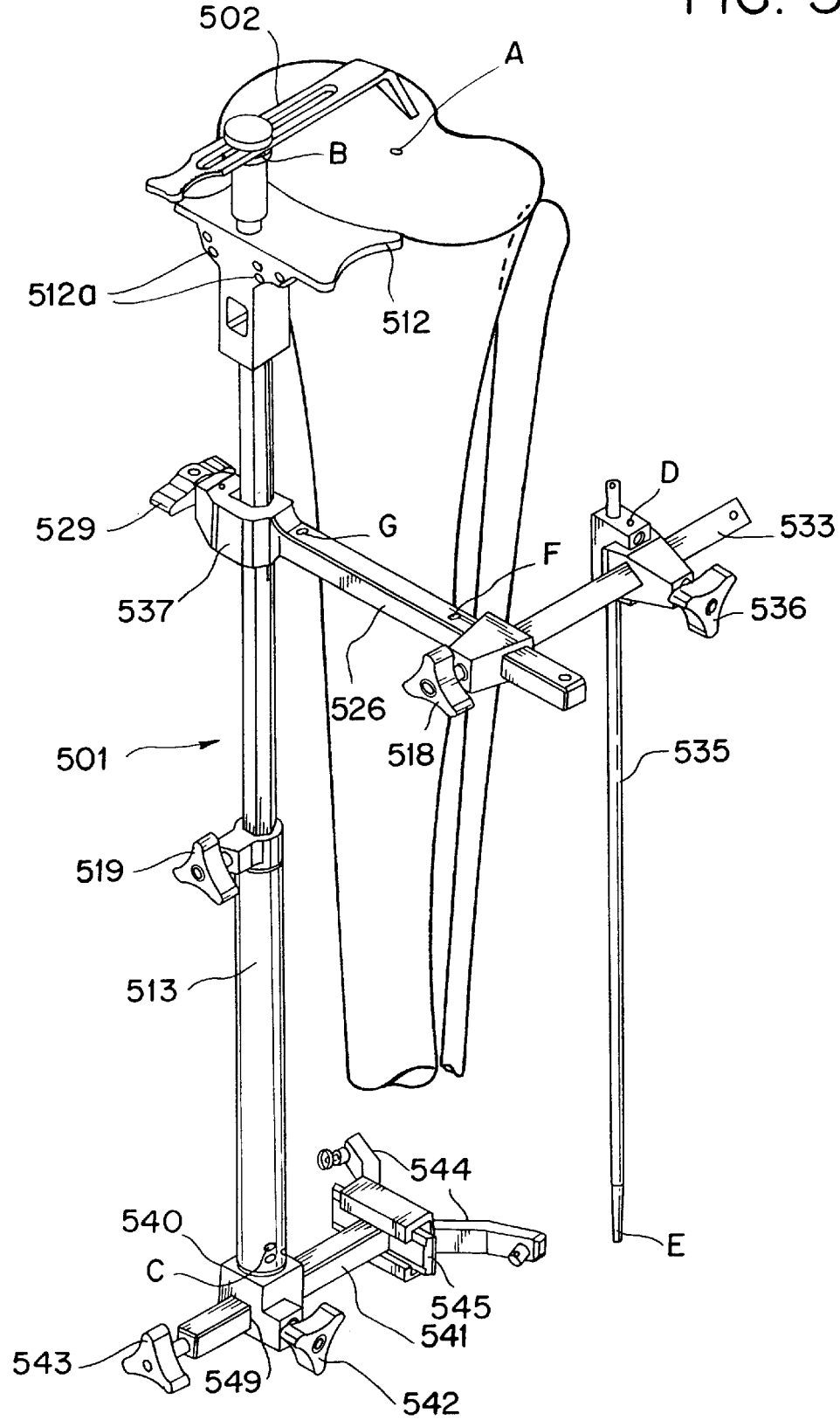
FIG. 5 is a perspective view of another type of Extra Medullary Tibial Resection Guide.

FIG. 5 shows another alternative embodiment of an extramedullary tibial resection guide. In this embodiment, the tibial resection guide is not anchored above the tibia. Instead, the first distally extending guide rod assembly (501) is anchored by pins inserted through the apertures (512a) in the cutting block (512) into the tibia. The first distally extending guide rod assembly (501) is comprised of three main elements: support arm (508), cutting block (512), and frontal telescoping rod (513).

In this embodiment, instead of a pivot block, a guide bar (502) is used to approximate the position of the intramedullary canal. The guide bar (502) has an elongated aperture (505) with which the position of the guide bar (502) may be adjusted to align the end of the guide bar (502) with approximately the intramedullary canal. When the guide bar (502) is in position, the guide bar (502) may be secured in place using a securing screw (510) which secures the guide bar (502) to the proximal end of the support arm (508). At the proximal end of the support arm is an adjustment screw (511) which is on a threaded rod (515) on the support arm (508). The cutting block (512) has several apertures (512a) extending through the cutting block (512) for inserting pins to secure the first distally extending guide rod assembly (501) in a position along the tibia based on where the surgeon determines the cut should be made. A stylus (502) is used to set the depth of the cut at the level desired by the surgeon.

The support rod (508) is attached at its distal end to a frontal telescoping rod (513) which can be used to adjust the length of the first distally extending guide rod assembly (501). The frontal telescoping rod (513) can be fixed at a length determined by the surgeon by tightening a thumbscrew (519). optionally, the distal end of the telescoping rod (513) may be secured to the ankle through an ankle clamp assembly such that an ankle clamp (540) is affixed to the distal end of the telescoping rod (513). The ankle clamp (540) is adjustable to contact the ankle by sliding the ankle clamp rod (541) through an aperture (549) and can be fixed in place by tightening a thumbscrew (542). The ankle clamp attachments (544) can be horizontally moved on the end (545) of ankle clamp rod (541) to best adjust to the ankle and can be fixed in place with a thumbscrew (543).

The second distally extending guide rod assembly (550) is made up of several parts, including: side bar (526); connection (537); top bar (533); rod anchoring block (534); and an extending rod (535). The second distally extending guide rod assembly (550) has a side bar (526) with a first end and second end.

The side bar (526) is connected to the first distally extending guide rod assembly (501) at its first end through a connection (537) that may be a c-clamp connection such as that described in the FIG. 1 embodiment or a dovetail connection such as that described in the FIG. 2 embodiment.

At its second end, the side bar (526) is connected to top bar (533), which extends perpendicularly in the transverse plane from the side bar (526), the transverse plane being defined by points D, F, and G. The top bar (533) has a first end and a second end. The first end of the top bar (533) is connected to the side bar (526). The top bar (533) may slide back and forth on the side bar (526) in the coronal plane to adjust the distance of the top bar (533) from the leg of the patient. The coronal reference plane being defined by points A, located on the approximate center of the tibial plateau, D, and E.

The top bar (533) may be secured at a position on the side bar (526) by tightening a thumbscrew (518) or a similar functioning lever arm. Proximate the second end of the top bar (533) a rod anchoring block (534) is connected thereto. The rod anchoring block (534) may slide on the top bar (533) to adjust its position thereon.

The proximal end of an extending rod (535) which extends downwardly perpendicular to the top bar (533) is slidably coupled to the proximal end of the rod anchoring block (534). In order to facilitate the placement of the distal end of the extending rod (535) adjacent the malleolus, the surgeon may slide the top bar (533) along the side bar (526) and/or slide the rod anchoring block (534) along the top bar (533) which merely varies the position of the distal end of the extending rod (535) and does not affect any other parameter. When the distal end of the extending rod (535) is brought in close proximity to the approximate center of the malleolus on the lateral face of the distal end of the tibia, thumbscrews (518) and (536) may be tightened to secure the position of the extending rod (535).

Figure 6:
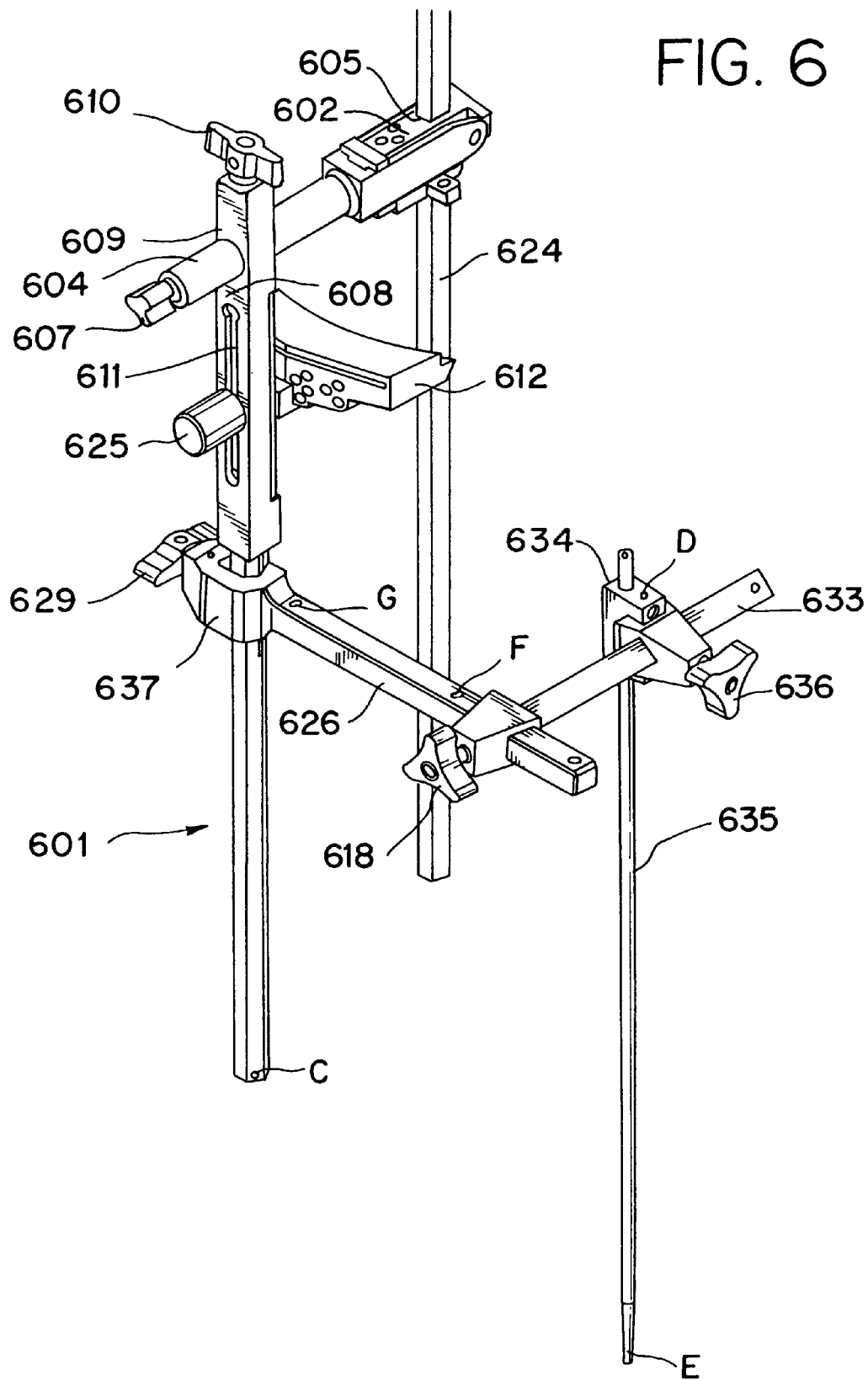
FIG. 6 is a perspective view of one type of Intra Medullary Tibial Resection Guide.

FIG. 6 shows a preferred embodiment of an intramedullary tibial resection guide. In this embodiment, an intramedullary rod (624) anchors the assembly to the approximate center of the top of the tibia. The first distally extending guide rod assembly (601) is composed of five main elements: pivot block (602), pivot arm (604), support arm (608), cutting block (612), and frontal telescoping rod (not shown) such as that in FIG. 2.

In this embodiment the intramedullary rod (624) runs through the pivot block (602) at a hole or aperture (605). The pivot block (602) itself is pivotally attached to the posterior end of the pivot arm (604) near a hinge point (606), which allows rotation of the pivot arm about the axis in the direction of the sagittal plane. Optionally, the intramedullary rod (624) and the aperture (605) may be sized and dimensioned so that the pivot block (602) and attached pivot arm (604) can swivel about hole (605) after the insertion of the intramedullary rod (624). After the surgeon has positioned the cutting block (612) in close proximity to the front of the tibia, a secondary anchor pin (not shown) is placed in secondary hole or aperture (603) to secure the entire first distally extending guide rod assembly (601) in place. At the anterior end of the pivot arm (604), a thumbscrew or lever (607) can be turned to tighten the grip of the pivot arm (604) against the pivot block (602).

The pivot arm (604) itself fits through an aperture (609) near the proximal end of the support arm (608). The pivot arm (604) extends through aperture (609) of the support arm (608) and may slide back and forth on the pivot arm (604), is tightened against the pivot arm by a thumbscrew (610) or similarly functioning lever located adjacent the aperture (609). The support arm (608) has an elongated aperture (611) in the approximate center of the support arm (608). A screw (625) fits through the elongated aperture (611) and allows for the tightening of the cutting block (612) against the support arm (608). This allows the cutting block (612) to be stabilized at an optimal position along the tibia based on where the surgeon determines the cut should be made. A stylus (not shown) is used to set the depth of the cut at the level desired by the surgeon.

The support arm (608) may be attached at its distal end to a frontal telescoping rod (not shown) such as that in FIG. 2 which can adjust the length of the first distally extending guide rod assembly (601).

The second distally extending guide rod assembly (650) is made up of several parts, including: side bar (626); connection (637); top bar (633); rod anchoring block (634); and an extending rod (635). The second distally extending guide rod assembly (650) has a side bar (626) with a first end and second end.

The side bar (626) is connected to the first distally extending guide rod assembly (601) at its first end through a connection (637) that may be a c-clamp type connection such as that shown. Alternatively, side bar (626) may have a dovetail connection (such as in FIG. 2 (217)) to engage grooves (see FIG. 2 (238)) of the support arm (608) below the cutting block (612). With this variation, the anterior half and posterior half of the grooved members (see FIG. 2, grooved members (227) and (228)) are connected to a thumbscrew or lever arm such that turning the thumbscrew or activating the lever arm causes the anterior half and posterior half to close on the dovetail connection of the side bar, gripping it in place.

At its second end, the side bar (626) is connected to top bar (633), which extends perpendicularly in the transverse plane from the side bar (626), the transverse plane being defined by points D, F, and G. The top bar (633) has a first end and a second end. The first end of the top bar (633) is connected to the side bar (626). The top bar (633) may slide back and forth on the side bar (626) in the coronal plane to adjust the distance of the top bar (633) from the leg of the patient. The coronal reference plane being defined by points A, D, and E. Point A lies on the approximate center of the tibial plateau at the top of the tibia. Point D lies at the top of a rod anchoring block (634). Point E lies at the distal end of an extending rod (635), at the approximate center of the malleolus.

The top bar (633) may be secured at a position on the side bar (626) by tightening a thumbscrew (618) or a similar functioning lever arm. Proximate the second end of the top bar (633) a rod anchoring block (634) is connected thereto. The rod anchoring block (634) may slide on the top bar (633) to adjust its position thereon.

The proximal end of an extending rod (635) which extends downwardly perpendicular to the top bar (633) is slidably coupled to the proximal end of the rod anchoring block (634). In order to facilitate the placement of the distal end of the extending rod (635) adjacent the malleolus, the surgeon may slide the top bar (633) along the side bar (626) and/or slide the rod anchoring block (634) along the top bar (633) which merely varies the position of the distal end of the extending rod (635) and does not affect any other parameter. When the distal end of the extending rod (635) is brought in close proximity to the approximate center of the malleolus on the lateral face of the distal end of the tibia, thumbscrews (618) and (636) may be tightened to secure the position of the extending rod (635).

The first distally extending guide rod assembly is positioned against the tibia in the sagittal plane. After tamping of the securing pins of FIG. 1 into the top of the tibia, placement of the primary anchor pin of FIG. 2 through the pivot block aperture into the intramedullary canal, or placement of the intramedullary rod through the pivot block aperture into the intramedullary canal, the first distally extending guide rod assembly is positioned in close proximity to the anterior face of the tibia with the cutting block touching the patient's leg. Optimal placement of the second distally extending guide rod assembly in the sagittal plane can vary due to surgeon preference. The lateral side of the knee is preferred in order to reference the fibular axis. In the embodiments of FIG. 6 and FIG. 2, once the pivot block is positioned, the secondary anchoring pin is placed into the bone to stabilize and prevent any rotation of the pivot block. In one aspect of the present invention, the support arm is attached to the pivot arm prior to placement of the pivot block into the bone. In another aspect of the invention, the support arm is attached to the pivot arm after placement of the pivot block into the bone.

After the pivot block is secured by an anchoring pin inserted through aperture in pivot block and the first distally extending guide rod assembly is attached, the frontal telescoping rod is extended downward and the end of the rod is placed directly over the talus. The angle formed between the plane defined by points A, B, C and the cutting block is preferably constant. The cutting block is removably attached to the support arm; hence, rotation of one causes equal rotation of the other.

Additionally, due to the fixed angular relationship between the extending rod and the cutting block, varying the flexion/extension angle of the cutting block also varies the flexion/extension angle of the side extending rod by the same amount. Thus, in order to locate the distal end of the side rod in close proximity to the malleolus, the surgeon may vary the flexion/extension angle of the cutting block.

After all alignments are made, the surgeon may wish to reassess one or more of the set angles and/or reference points and/or anchoring pin locations, according to personal preference and/or patient anatomy. Then, a plurality of stabilizing pins (not shown) are inserted into the anterior portion of the tibia through selected stabilizing pin apertures in the cutting block. The cutting block is then detached from the first distally extending guide rod assembly and both frame assemblies are removed, leaving behind only the cutting block. A proper tibial plateau resection plane for a saw blade to follow is thereby referenced by the top of the cutting block.

In another embodiment of the invention, the second distally extending guide rod assembly is configured and dimensioned so as to be attachable to an existing tibial resection guide assembly. The existing tibial resection guide may be any device attachable to the tibia which extends in the sagittal plane and contains a cutting block disposed generally perpendicular to the guide, such as those disclosed in U.S. Pat. No. 5,451,228 or U.S. Pat. No. 4,524,766, described above.

The invention described and claimed herein is not to be limited in scope by the specific embodiments herein disclosed since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

A number of references are cited herein, the entire disclosures of which are incorporated herein, in their entirety, by reference.

What is claimed is:

1. A tibial resection guide comprising: a first distally extending guide rod assembly having a first and second end, coupled with a second distally extending guide rod assembly, said second rod assembly is configured and dimensioned so as to be releasably coupled to said first rod assembly between the first and second end of said first rod assembly, wherein said tibial resection guide is oriented in the sagittal reference plane, and has a cutting block connected to the first rod assembly.

2. A tibial resection guide for aligning the tibial plateau with the mechanical axis of the tibia comprising:
   (a) a first distally extending guide rod assembly having a first and second end, said first end is attachable to the tibia, wherein said first distally extending guide rod assembly has a cutting block coupled thereto; and
   (b) a second distally extending guide rod assembly comprising a top bar positioned below the first end of the first distally extending guide rod and an extending rod slidably coupled to a rod anchoring block, said rod anchoring block slidably coupled to said top bar, said top bar slidably coupled to a side bar, said extending rod extending toward the ankle to a point below the tibial plateau, said second distally extending guide rod assembly configured and dimensioned so as to be removably coupled to a support arm of the first distally extending guide rod assembly.

3. The apparatus of claim 2 wherein the proximal end of the first distally extending guide rod assembly is set at a fixed relative angle of 90 degrees to the proximal end of the second distally extending guide rod assembly.

4. The apparatus of claim 2 wherein the top bar and the side bar are set a fixed relative angle of 90 degrees to each other.

5. A tibial resection guide for aligning the tibial plateau with the mechanical axis of the tibia comprising
   (a) a first distally extending guide rod assembly having a first and second end which is attachable to the tibia and comprised of a block having at least one hole; a support arm which is coupled to the block which extends downward from and is slidably coupled to the block; a cutting block which is removably coupled to the support arm; and a frontal telescoping rod which is coupled to the support arm; and
   (b) a second distally extending guide rod assembly comprising a top bar, an extending rod transverse and slidably coupled to a rod anchoring block, said rod anchoring block slidably coupled to said top bar, said top bar slidably coupled to a side bar, said second distally extending guide rod assembly configured and dimensioned so as to be releasably coupled to the first distally extending guide rod assembly between the first and second end.

6. The apparatus of claim 5 further comprising at least one anchoring pin dimensioned to fit through a hole in the block.

7. The apparatus of claim 5 further comprising at least one primary anchoring pin attached to the block.

8. The apparatus of claim 5 further comprising a block which is a pivot block having a primary hole and a secondary hole adjacent to the primary hole; a pivot arm which is pivotally coupled to the pivot block at a hinge which permits the pivot arm to move in the sagittal plane; a primary anchoring pin dimensioned to fit through the primary hole in the pivot block and a secondary anchoring pin dimensioned to fit through the secondary hole in the pivot block.

9. The apparatus of claim 5 further comprising a tightening means operatively associated with the support arm to selectively lock the slidable support arm in a selected position on the pivot arm.

10. The apparatus of claim 5 wherein the support arm has an elongated longitudinal aperture and the cutting block is coupled to the support arm by means of a screw which passes through the elongated aperture.

11. The apparatus of claim 5 wherein the cutting block contains one or more holes for insertion of one or more stabilizing pins therethrough for securing the cutting block to the tibia.

12. The apparatus of claim 2 wherein the first distally extending guide rod assembly includes a pivot block; the side bar of the second distally extending guide rod assembly is removably coupled at its proximal end below the cutting block of the first distally extending guide rod assembly; and the extending rod of the second distally extending guide rod assembly extends downwardly from the top bar of the second distally extending guide rod assembly.

13. The apparatus of claim 12 wherein the side bar of the second distally extending guide rod assembly couples to the support arm by a dovetail or groove.

14. The apparatus of claim 12 wherein the side bar of the second distally extending guide rod assembly couples to the support arm by an aperture that is configured and dimensioned to have a mating geometry with that of the support arm.

15. A tibial resection guide for aligning the tibial plateau with the mechanical axis of the tibia comprising (a) a first distally extending guide rod assembly having a first and second end which is attachable to the tibia and comprised of a pivot block having an orifice to removably accept an elongated rod that is formed to include a first end that is adapted to be inserted into a medullary canal in the tibia bone and a second end that extends upwardly out of the tibia bone when the first end is inserted into the bone, said second end removably coupled to said pivot block; a pivot arm which is pivotally coupled to the pivot block at a hinge which permits the pivot arm to swivel in the sagittal plane; a support arm which extends downward from and is slidably coupled to the pivot arm; a cutting block which is removably coupled to the support arm; and a frontal telescoping rod which is coupled to the support arm; and (b) a second distally extending guide rod assembly comprising a top bar, an extending rod transverse and slidably coupled to a rod anchoring block, said rod anchoring block slidably coupled to said top bar, said top bar slidably coupled to a side bar, said second distally extending guide rod assembly configured and dimensioned so as to be removably coupled to the support arm of the first distally extending guide rod assembly between the first and second end.

16. The apparatus of claim 15 further comprising a tightening means operatively associated with the support arm to selectively lock the slidable support arm in a selected position on the pivot arm.

17. The apparatus of claim 15 wherein the support arm has an elongated longitudinal aperture therethrough and the cutting block is coupled to the support arm by means of a screw which passes through the elongated aperture.

18. The apparatus of claim 15 wherein the cutting block contains one or more holes for insertion of one or more stabilizing pins therethrough for securing the cutting block to the tibia.

19. The apparatus of claim 15 wherein the side bar of the second distally extending guide rod assembly attaches to the support arm by means of a dovetail or groove.

20. The apparatus of claim 15 wherein the side bar of the second distally extending guide rod assembly attaches to the support arm by means of an aperture that is configured and dimensioned to have a mating geometry with that of the support arm.

21. A method for positioning the tibial resection cutting block of claim 5 which comprises:

(a) anchoring a block of a first distally extending guide rod assembly to the tibial plateau using at least one anchoring pin, said first distally extending guide rod assembly having a cutting block attached thereto;

(b) attaching a second distally extending guide rod assembly to the first distally extending guide rod assembly;

(c) extending a frontal telescoping rod downwardly from the distal end of the first distally extending guide rod assembly so that it is positioned adjacent the anterior face of the distal end of the tibia;

(d) extending a side extending rod downwardly from the distal end of the second distally extending guide rod assembly so that it is positioned adjacent the lateral face of the distal end of the tibia;

(e) inserting at least one pin through an aperture of the cutting block to secure the cutting block to the tibia; and (f) removing the first distally extending guide rod assembly and the second distally extending guide rod assembly from the cutting block.

22. A method for positioning the tibial resection cutting block of claim 15 which comprises:

(a) inserting one end of an elongated rod into the medullary canal in the tibial bone and removably attaching the other end to a first distally extending guide rod assembly, said first distally extending guide rod assembly including a removable cutting block having plurality of apertures therethrough;

(b) attaching a second distally extending guide rod assembly to the first distally extending guide rod assembly;

(c) extending a side extending rod downwardly from the distal end of the second distally extending guide rod assembly so that it is positioned adjacent the medial face of the distal end of the tibia;

(d) inserting a plurality of pins through the cutting block apertures to secure the cutting block to the tibia; and (e) removing the elongated rod from the medullary canal and the first distally extending guide rod assembly and the second distally extending guide rod assembly from the cutting block.

* * * * *

UNITED STATES PATENT AND TRADEMARK OFFICE
CERTIFICATE OF CORRECTION

PATENT NO. : 6,090,114
DATED : July 18, 2000
INVENTOR(S) : Matsuno et al.

It is certified that error appears in the above-identified patent and that said Letters Patent is hereby corrected as shown below:

On the face of the patent,
In the title, cancel the word "Plateau".

Column 1, line 1, cancel the word "Plateau".

Signed and Sealed this

Seventeenth Day of April, 2001

*Attest:*

NICHOLAS P. GODICI

*Attesting Officer*   *Acting Director of the United States Patent and Trademark Office*

UNITED STATES PATENT AND TRADEMARK OFFICE
CERTIFICATE OF CORRECTION

PATENT NO. : 6,090,114
DATED : July 18, 2000
INVENTOR(S) : Matsuno et al.

It is certified that error appears in the above-identified patent and that said Letters Patent is hereby corrected as shown below:

<u>Title page, Item [73],</u>
Line 1, cancel "Stryker"

Signed and Sealed this

Thirteenth Day of November, 2001

*Attest:*

*Attesting Officer*

NICHOLAS P. GODICI
*Acting Director of the United States Patent and Trademark Office*